US 6,485,478 B2

(12) United States Patent
Imai et al.

(10) Patent No.: US 6,485,478 B2
(45) Date of Patent: Nov. 26, 2002

(54) DISPOSABLE UNDERGARMENT

(75) Inventors: Shigeo Imai, Kagawa-ken (JP); Toshimitsu Baba, Kagawa-ken (JP)

(73) Assignee: Uni-Charm Corporation, Ehime-ken (JP)

( * ) Notice: Subject to any disclaimer, the term of this patent is extended or adjusted under 35 U.S.C. 154(b) by 0 days.

(21) Appl. No.: 09/864,729

(22) Filed: May 24, 2001

(65) Prior Publication Data

US 2001/0049515 A1 Dec. 6, 2001

(30) Foreign Application Priority Data

May 29, 2000 (JP) ........................................ 2000-158246

(51) Int. Cl.[7] ............................ A61F 13/20; A61F 13/15
(52) U.S. Cl. .......................... 604/385.13; 604/385.01; 604/385.24; 604/386; 604/387; 604/391; 604/385.03
(58) Field of Search ........................... 604/385.13, 391, 604/385.24, 385.01, 386, 387, 385.03

(56) References Cited

U.S. PATENT DOCUMENTS

| | | | | |
|---|---|---|---|---|
| 4,604,096 A | * | 8/1986 | Dean et al. | 604/385.13 |
| 4,605,403 A | * | 8/1986 | Tucker | 604/385.13 |
| 5,403,302 A | * | 4/1995 | Roessler et al. | 604/385.13 |
| 5,531,732 A | * | 7/1996 | Wood | 604/385.13 |
| 5,653,704 A | * | 8/1997 | Buell et al. | 604/373 |
| 5,688,258 A | * | 11/1997 | Rawat et al. | 604/358 |
| 5,762,645 A | | 6/1998 | Peck et al. | |
| 5,897,546 A | * | 4/1999 | Kido et al. | 24/442 |
| 6,030,372 A | | 2/2000 | Buell et al. | |
| 6,063,067 A | * | 5/2000 | Takizawa et al. | 24/452 |

FOREIGN PATENT DOCUMENTS

| | | | |
|---|---|---|---|
| EP | 0880956 A2 | * 2/1998 | ............ A61F/13/15 |
| EP | 0 880 956 A2 | 12/1998 | |
| EP | 0 951 888 A2 | 10/1999 | |
| JP | 9-38139 | 2/1997 | |
| JP | 9-181908 | 7/1997 | |
| JP | 10-309299 | 11/1998 | |
| JP | 10-328237 | 12/1998 | |

OTHER PUBLICATIONS

Copy of European Search Report dated May 24, 2002.

* cited by examiner

Primary Examiner—William C. Doerrler
Assistant Examiner—Filip Zec
(74) Attorney, Agent, or Firm—Baker & Daniels

(57) ABSTRACT

A disposable undergarment that has a pair of tape fasteners attached to transversely opposite side edge portions of a rear waist region and a non-stretchable target tape strip attached to the outer surface of a front waist region. The front and rear waist regions and a crotch region are elastically stretchable in length and width. The tape strip includes a flexible plastic sheet having transversely opposite side edges extending longitudinally and upper and lower edges extending transversely of the undergarment and a plurality of long fibers extending longitudinally on the outer surface of the sheet between the upper and lower edges. The sheet is formed with a plurality of perforated lines arranged to be transversely spaced one from another by a predetermined dimension and to extend between the vicinity of the upper edge and the vicinity of the lower edge. The target tape strip is attached to the front waist region being substantially in non-stretched state. The long fibers are bonded to the sheet by means of sealing zones transversely extending in the vicinity of the upper and lower sides of the sheet.

5 Claims, 5 Drawing Sheets

DISPOSABLE UNDERGARMENT

BACKGROUND OF THE INVENTION

This invention relates to a disposable undergarment such as a disposable diaper, a diaper cover, a training pant or an incontinent pant.

Connectional disposable diapers of open-type are provided with tape fasteners transversely extending outward from transversely opposite side edges of a rear waist region and a target tape strip attached to outer surface of a front waist region. In an example of such diaper, hook and loop members of the mechanical fastener known by the trade name such as MAGIC TAPE or VELCRO are used as the tape fastener and the target tape strip, respectively. Specifically, the hook member is attached to the inner surface of each base tape strip and a rectangular strip of the loop member is attached to the outer surface of the front waist region at a desired position to form a landing zone. The tape fasteners are detachably anchored on the target tape strip to connect the front and rear waist regions of the diaper to each other.

Such diaper is disclosed, for example, in Japanese Patent Application Publication Nos. 1997-38139A, 1997-191908A, 1998-309299A and 1998-328237A. The diaper disclosed in these Publications uses a non-stretchable loop member as the target tape strip.

With the diaper having an elastic stretchability, it is assumed that the non-stretchable loop member serving as the target tape strip is attached to the front waist region which is substantially in its non-stretched condition. In this case, the target tape strip will restrict a stretchability of the front waist region in its zone provided with the target tape strip. Consequently, the diaper will be derived of its stretchability in the zone thereof provided with the target tape strip.

SUMMARY OF THE INVENTION

It is an object of this invention to provide a disposable undergarment having an elastic stretchability so that, if a non-stretchable target tape strip is attached to the outer surface of the substantially non-stretched front waist region, the front waist region may be kept stretchable even in the attachment zone of the target tape strip.

According to this invention, there is provided a disposable undergarment comprising a basic structure contoured by transversely opposite side edge portions longitudinally extending in parallel to each other and longitudinally opposite edge portions transversely extending in parallel to each other and having a front waist region to cover a wearer's belly, a rear waist region to cover the wearer s back and a crotch region extending between the waist regions, a pair of tape fasteners attached to transversely opposite side edge portions of the rear waist region and a non-stretchable target tape strip attached to outer surface of the front waist region so that the tape fasteners serve as male members adapted to be separably anchored on the target tape strip serving as a female member and thereby to connect the front and rear waist regions to each other.

According to this invention, of the front waist region, the rear waist regions and the crotch region, at least the front waist region is elastically stretchable at least transversely of the undergarment; the target tape strip comprises a flexible film layer having transversely opposite side edges extending longitudinally and upper and lower edges extending transversely of the undergarment and a plurality of long fibers extending longitudinally in parallel one to another on an outer surface of the film layer between upper and lower edges; the film layer is formed with a plurality of slits arranged to be transversely spaced one from another by a predetermined dimension and to extend longitudinally between a vicinity of the upper edge and a vicinity of the lower edge; the target tape strip is attached to the front waist region being substantially in non-stretched state; and the long fibers are bonded to the film layer in the vicinity of the upper and lower sides the film layer.

The expression "substantially in non-stretched state" used herein should be understood to include both the state in which the front waist region is not stretched at all and the state in which the front waist region is slightly stretched.

According to one embodiment of this invention, the long fibers are slackened outward from the outer surface of the film layer between the upper and lower edges of the film layer.

According to another embodiment of this invention, the film layer is formed with a plurality of perforated lines arranged to be transversely spaced one from another by a predetermined dimension and to extend between the vicinity of the upper edge and the vicinity of the lower edge so that the film layer is easily torn apart along the perforated lines to for the film layer with the slits.

According to still another embodiment of this invention, the film layer is bonded to the front waist region by means of plural stripes of adhesive arranged to be transversely spaced one from another and to extending longitudinally of the undergarment.

According to further another embodiment of this invention, the undergarment comprises a liquid-pervious topsheet to contact the wearer's skin, a liquid-impervious backsheet not to contact the wearer's skin and a liquid-absorbent core disposed therebetween.

DETAILED DESCRIPTION OF THE PREFERRED EMBODIMENTS

Details of the disposable undergarment according to this invention will be more fully understood from the description of a disposable diaper of open-type as a typical embodiment with reference to the accompanying drawings.

Figure 1:
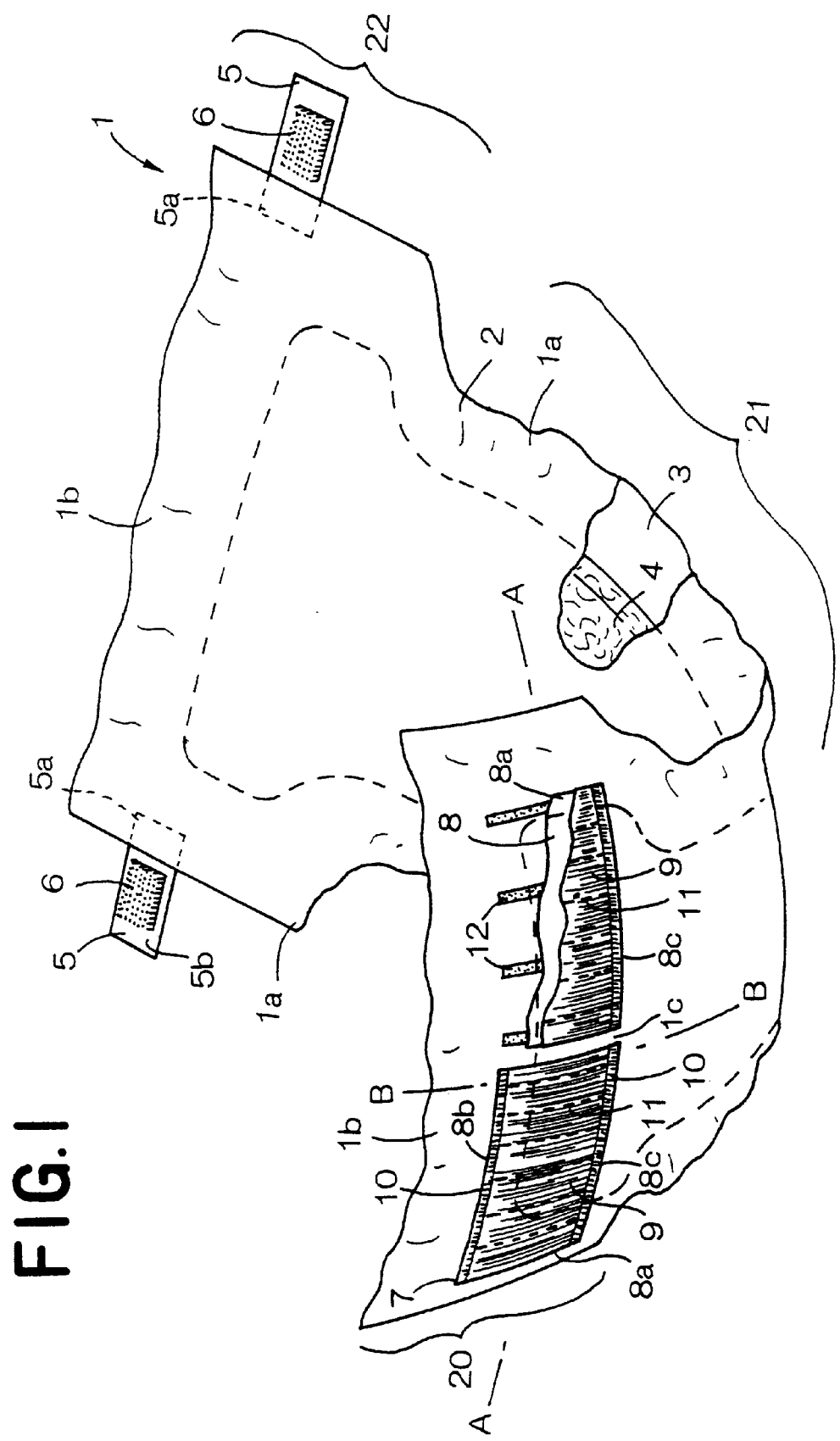
FIG. 1 is a perspective view showing a partially cutaway diaper.
Figure 2:
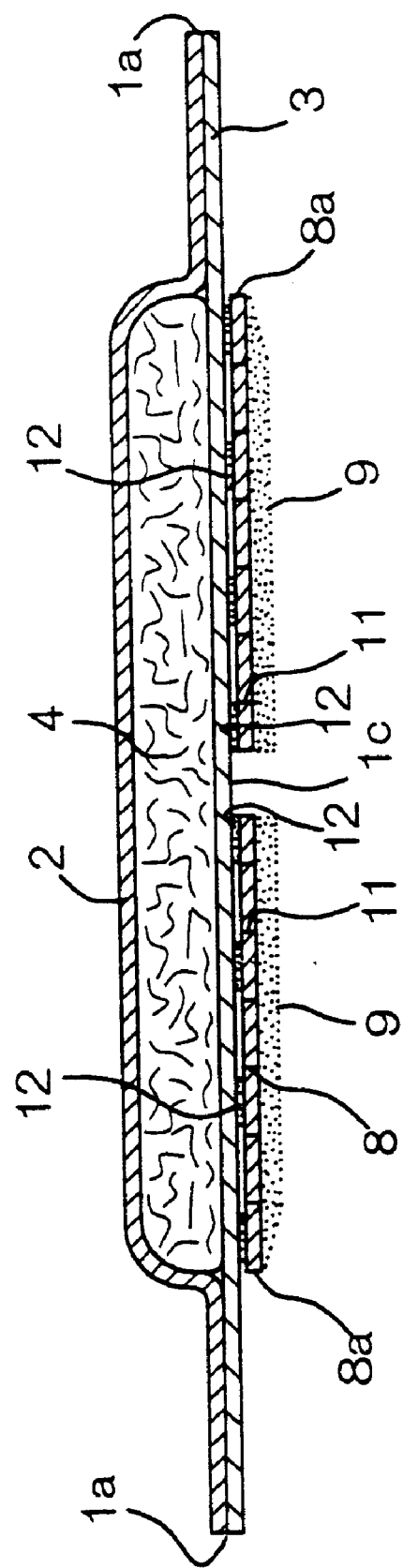
FIG. 2 is a sectional view showing the diaper of FIG. 1 taken along a line A—A in FIG. 1.
Figure 3:
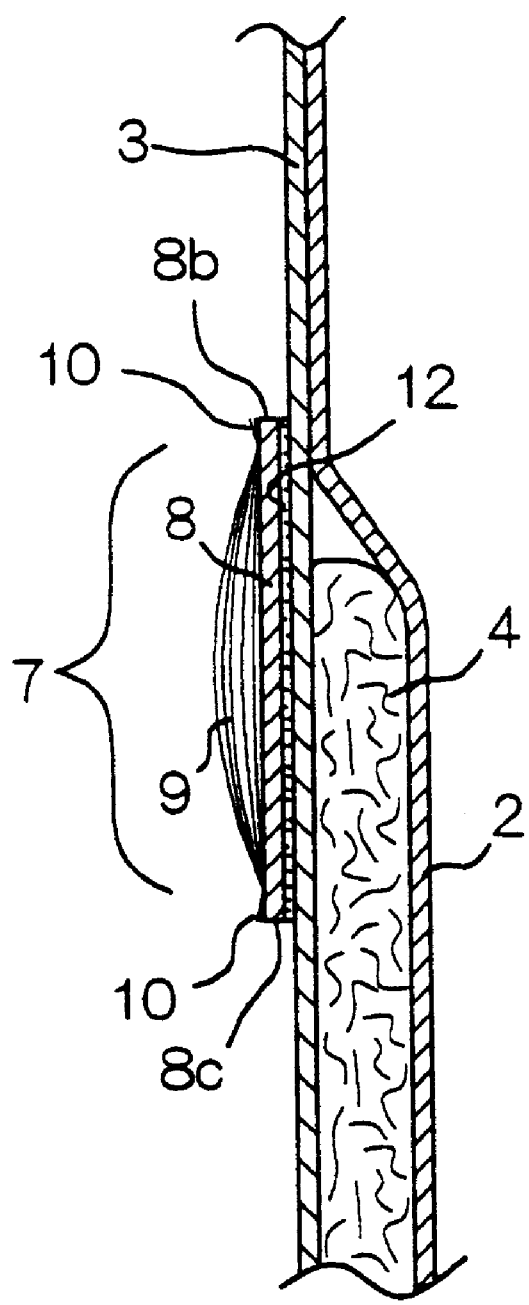
FIG. 3 is a sectional view showing the diaper of FIG. 1 taken along a line B—B in FIG. 1.

FIG. 1 is a perspective view showing a partially cutaway diaper 1, FIG. 2 is a sectional view taken along a line A—A in FIG. 1 and FIG. 3 is a sectional view taken along a line B—B in FIG. 1. The diaper 1 basically comprises a liquid-pervious topsheet 2, a liquid-impervious backsheet 3 and a liquid-absorbent core 4 disposed between the topsheet 2 and the backsheet 3 and bonded to the inner surface of the topsheet 2.

The diaper 1 has a front waist region 20 to cover a wearer's belly, a rear waist region 22 to cover the wearer's back and a crotch region 21 extending between the front and rear waist regions 20, 22. The diaper 1 is contoured by transversely opposite side edge portions 1a longitudinally extending in parallel to each other but, in the crotch region 21, curving inward transversely of the diaper 1 and longitudinally opposite end portions 1b transversely extending in parallel to each other.

Of the diaper 1, the topsheet 2 and the backsheet 3 are made of a nonwoven fabric being elastically stretchable both in length and width. Portions of the topsheet 2 and the backsheet 3 extending outward beyond a peripheral edge of the core 4 are placed upon and intermittently bonded to each other.

A pair of tape fasteners 5 are attached to the side edge portions 1a of the rear waist region 22 so as to extend transversely outward. In cooperation with these tape fasteners 5, a non-stretchable target tape strip 7 serving as a landing zone for the tape fasteners 5 is attached to the outer surface of the backsheet 3 in the front waist region 20. Specifically, the target tape strip 7 is divided into two sections about a central zone 1c of the front waist region 20.

Each of the tape fasteners 5 has its proximal end portion 5a disposed between the topsheet 2 and the backsheet 3 and firmly bonded to respective inner surfaces of these sheets 2, 3 by means of adhesive (not shown). A free end portion 5b of the tape fastener 5 is provided on its inner surface with a hook member 6 serving as one component of a mechanical fastener bonded to the inner surface by means of adhesive (not shown).

The target tape strip 7 comprises a transversely larger flexible plastic sheet 8 (film layer) having side edges 8a longitudinally extending in parallel to each other and upper and lower edges 8b, 8c transversely extending in parallel to each other, and a plurality of long fibers 9 longitudinally extending in parallel one to another on outer surface of the plastic sheet 8 between its upper and lower edges 8b, 8c.

The plastic sheet 8 is formed with a plurality of perforated lines 11 extending between the vicinity of the upper edge 8b and the vicinity of the lower edge 8c and transversely spaced one from another by a predetermined dimension.

The long fibers 9 are bonded to the plastic sheet 8 along the upper and lower edges 8b, 8c thereof by means of sealing lines 10 so that these long fibers 9 may be slackened outward from the outer surface of the plastic sheet 8 between the upper and lower edges 8b, 8c.

Of the target tape strip 7, the plastic sheet 8 is attached to the outer surface of the backsheet 3, which is in non-stretched condition, by means of a plural stripes of adhesive 12. These stripes of adhesive 12 are arranged to be transversely spaced one from another by a predetermined dimension and to extend longitudinally in the vicinity of the opposite side edges 8a and between each pair of the adjacent perforated lines 11 of the plastic sheet 8.

During nonuse of the diaper 1, the tape fasteners 5 are kept folded back upon the outer surface of the topsheet 2 and separably fixed thereto by means of the hook members 6 (not sown). During use of the diaper 1, the tape fasteners 5 are kept anchored on the outer surface of the target tape strip 7 by means of the hook members 6. The tape fasteners 5 are effectively anchored on the target tape strip 7 with the hook members 6 entering among the long fibers 9 so as to be engaged with the long fibers 9.

Figure 4:
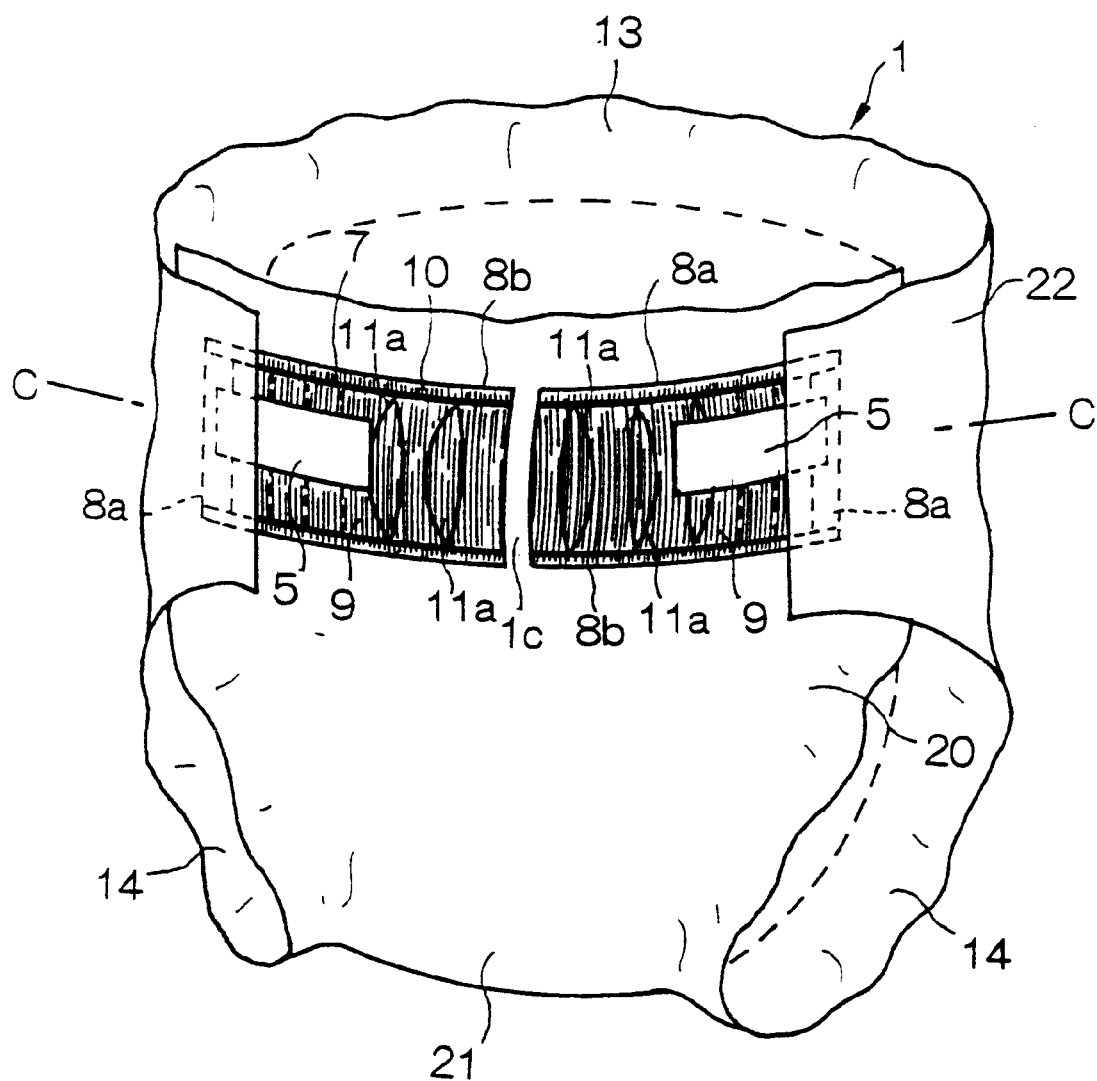
FIG. 4 is a perspective view showing the diaper of FIG. 1 with front and rear waist regions connected to each other to put it on a wearer's body.
Figure 5:
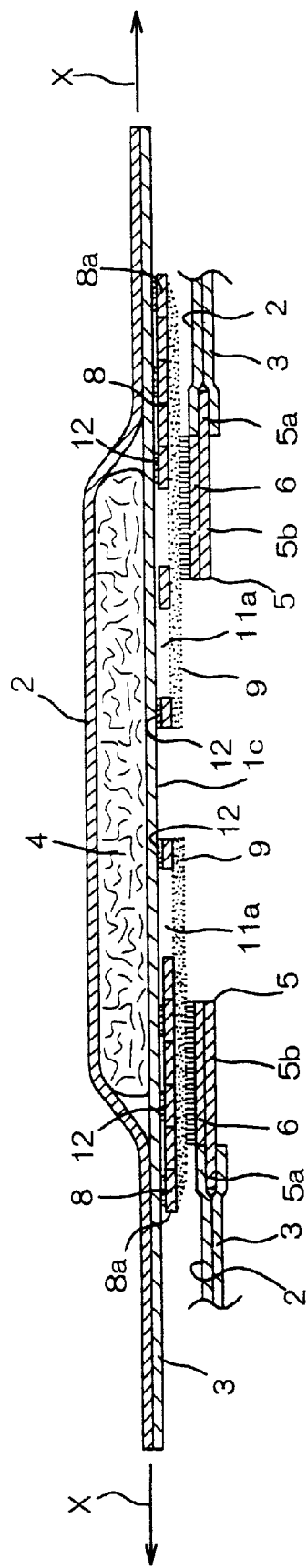
FIG. 5 is a sectional view taken along a line C—C in FIG. 4.

FIG. 4 is a perspective view showing the diaper 1 as put on a wearer's body with the front and rear waist regions 20, 22 being connected to each other and FIG. 5 is a sectional view taken along a line C—C in FIG. 4. Referring to FIG. 4, the respective inner surfaces of the tape fasteners 5 are separably anchored on the outer surface of the target tape strip 7 to form a waist-opening 13 and a pair of leg-openings 14. The front and rear waist regions 20, 22 are stretched transversely outward as indicated by an arrow X in FIG. 5 as the diaper is put on the wearer's body. Thereupon, the target tape strip 7 is also pulled transversely outward. The plastic sheet 8 of the target tape strip 7 is torn along the perforated lines 11 under tension exerted thereon transversely outward to form a plurality of slits 11a.

These slits 11a of the plastic sheet 8 are enlarged transversely outward as the top- and backsheets 2, 3 of the diaper 1 are stretched transversely outward and consequently each of the slits 11a defines a substantially elliptic space having its major axis extending longitudinally of the diaper 1. Both the topsheet 2 and the backsheet 3 can be stretched transversely outward by a dimension corresponding to the total dimension by which the slits 11a can be enlarged. In other words, an elastically stretchability of the topsheet 2 and the backsheet 3 in the entire zone provided with the target tape strip 7 is not restricted by this target tape strip 7. In this way, there is no anxiety that this zone of the topsheet 2 and the backsheet 3 might be completely deprived of the initial elastically stretchability thereof.

While the long fibers 9 are scattered transversely as the slits 11a of the target tape strip 7 are enlarged transversely, some of the long fibers 9 remain within each of the enlarged slits 11a. Therefore, it is not apprehended that the long fibers 9 of the target tape strip 7 might be interrupted even when the front waist region 20 is stretched transversely outward. The topsheet 2 and the backsheet 3 contract and the elliptic slits 11a are closed to restore their rectilinear shapes as the tape fasteners 5 and the target tape strip 7 are disengaged from each other.

The target tape strip 7 is divided in two sections along the central zone 1c of the front waist region 20 and portions of topsheet 2 and the backsheet 3 extending along the central zone 1c have their initial elastic stretchability free from any restriction by the target tape strip 7. Namely, the front waist region 20 is stretchable transversely outward in the central zone 1c of the front waist region 20.

The diaper 1 as herein described and illustrated is adapted to be transversely stretchable at a predetermined ratio as it is put on a wearer's body. The front and rear waist regions 20, 22 and the crotch region 21 are transversely stretchable from the non-stretched state thereof preferably at a ratio of 30~200%.

While the target tape strip 7 has been described to be attached to the non-stretched front waist region 20, it is also possible to attach the target tape strip 7 to the front waist region 20 being slightly stretched. The expression "being slightly stretched" means that the front waist region is transversely stretched at a ratio exceeding 0% but less than 30%.

While the dimension by which the perforated lines 11 are transversely spaced one from another as well as the number of these perforated lines 11 are not particularly specified, it is preferable for the diaper I that the dimension is relatively small and the number is relatively large. The larger the number of the perforated lines 11, the larger the dimension by which the target tape strip 7 can be stretched transversely outward and also the larger the dimension by which the zone of the front waist region 20 provided with the target tape strip 7 can be stretched transversely outward.

It is unnecessary for the stripes of adhesive 12 to extend fully between respective pairs of the adjacent perforated lines 11 but it is preferable that they are transversely spaced one from another by a desired dimension. In other words, the plastic sheet 8 may be attached to the backsheet 3 by means of the stripes of adhesive 12 arranged discontinuously in the transverse direction. The strips of adhesive 12 are preferably formed by elastically or inelastically stretchable adhesive.

It is also possible to form the backsheet 3 using nonwoven fabric having a transversely elastic stretchability and to form the topsheet 2 using a non-stretchable nonwoven fabric. In this case, the topsheet 2 may be placed upon the backsheet 3 being stretched transversely outward and then the portions of these sheets 2, 3 extending longitudinally as well as transversely outward beyond the peripheral edge of the core 4 are intermittently bonded to each other.

The target tape strip 7 is not limited to that divided in two sections about the central zone 1c of the front waist region 20 and may also extend transversely on the outer surface of the front waist region 20 without interruption. The perforated lines 11 of the plastic sheet 8 may be replaced by a plurality of slits 11a arranged to be transversely spaced one from another by a predetermined dimension and to vertically extend between the vicinity of the upper edge 8b and the vicinity of the lower edge 8c of the plastic sheet 8.

Though not shown, it is also possible to fuse and then harden the long fibers so that some of these long fibers may be partially converted to a film layer and the remaining long fibers may be integrated with the film layer and to use such integrated material as the target tape strip. In this target tape strip, the remaining long fibers are heat-sealed with the film layer along upper and lower edges of this film layer. In the case of such target tape strip, the film layer may be formed with a plurality of perforated lines or slits. Then, the film layer may be bonded to the outer surface of the backsheet by means of plural stripes of adhesive arranged to be transversely spaced one from another by a predetermined dimension and to extend longitudinally in the vicinity of the transversely opposite side edges and between respective pairs of the adjacent perforated lines or slits.

The topsheet 2 is preferably formed from an inelastic or an elastic nonwoven fabric treated to become hydrophilic. An inelastic or elastic porous plastic film also may be used for stock material for the topsheet 2.

The backsheet 3 may be formed from an elastic nonwoven fabric, an elastic plastic film or a laminated sheet of these plastic film and nonwoven fabric. It is also possible to form the backsheet 3 from a composite sheet comprising an inelastic plastic film, an inelastic nonwoven fabric and an elastomeric sheet such as natural or synthetic rubber or elastic threads both having an elastic stretchability disposed between the plastic film and nonwoven fabric. The nonwoven fabric used to form the backsheet 3 is preferably hydrophobic.

The nonwoven fabric used for this invention may be selected from a group including those of spun lace-, needle punch-, melt blown-, thermal bond- spun bond- and chemical bond-types.

The plastic sheet 8 may be made of flexible thermoplastic synthetic resin such as polyethylene or polypropylene, polyester.

The long fibers 9 are obtained by filamentation of tow consisting of plural filaments into the form of web and preferably crimped to facilitate the hook member of the tape fastener to come in engagement with these long fibers 9. The filaments preferably have a fineness of 0.5~70 Dtex and a basis weight of 20~150 g/m$^2$.

The filament may be selected from a group including polyolefine-, polyester- or polyamide-based fiber, or core-sheath type conjugated fiber of polyethylene/polypropylene, polyethylene/polyester or polyethylene/polyethylene terephthalate.

The core 4 comprises a mixture of fluff pulp obtained by crushing wood pulp and high absorption polymer particles compressed to a desired thickness and entirely covered with a water-pervious sheet (not shown) such as liquid-diffusive tissue paper. The high absorption polymer may be selected from a group including graft polymerized starch, modified cellulose, water-soluble crosslinked polymer and alkali metal acrylate of self-crosslinking type.

Bonding or attachment of the sheets 2, 3 and the core 4 may be carried out using hot melt adhesive, pressure-sensitive adhesive or heat-welding technique.

This invention is applicable to not only the disposable diaper 1 but also to a diaper cover, a training pant or an incontinent pant.

The disposable undergarment according to this invention inelastically stretchable in length and width, at least in width. With such undergarment, it is assumed that the non-stretchable target tape strip is attached to the outer surface of the front waist region being substantially not stretched. Even in this case, it is not apprehended that the zone of the front waist region in which the target tape has been attached to the front waist region might be completely deprived of its initial stretchability. This is for the reason that the film layer of the target tape strip is formed with a plurality of slits each extending longitudinally of the article.

Each of the slits formed in the film layer is transversely enlarged in a substantially elliptic space having its major axis oriented longitudinally of the article. As a result, the zone of the front waist region in which the target tape strip has been attached thereto can be stretched by a dimension corresponding to a total dimension by which the slits of the film layer can be transversely enlarged.

While the long fibers are transversely scattered as the slits are transversely enlarged, some of the long fibers still remain within each elliptic space defined by the enlarged slit. Consequently, there is no anxiety that the long fibers on the target tape strip might be interrupted even when the front waist region is stretched transversely outward. In this way, the tape fastener can be effectively engaged with the target tape strip at any position of this tape strip.

What is claimed is:

1. A disposable undergarment comprising:

transversely opposite side edge portions longitudinally extending in parallel to each other;

longitudinally opposite edge portions transversely extending in parallel to each other;

a front waist region;

a rear waist region;

a crotch region extending between said front and rear waist regions;

a pair of tape fasteners attached to said transversely opposite side edge portions along said rear waist region; and a non-stretchable target tape strip attached to an outer surface of said front waist region, said target tape strip serving as a female member and said tape fasteners serve as male members adapted to be separably anchored on said target tape strip to thereby connect said front and rear waist regions to each other, of said front waist region, said rear waist region and said crotch region, at least said front waist region is elastically stretchable at least transversely of the undergarment, said target tape strip comprising:
- a flexible film layer having transversely opposite side edges extending longitudinally and upper and lower edges extending transversely of the undergarment; and
- a plurality of long fibers extending longitudinally in parallel one to another on an outer surface of said flexible film layer between the upper and lower edges,
- said flexible film layer being formed with a plurality of slits arranged so as to be transversely spaced apart one from another and to extend longitudinally between a vicinity of the upper edge and a vicinity of the lower edge;
- said target tape strip being attached to said front waist region substantially in a non-stretched state,
- said plurality of long fibers being bonded to said flexible film layer in the vicinity of the upper and lower sides of said flexible film layer.

2. The undergarment according to claim 1, wherein said plurality of long fibers are slackened outward from the outer surface of said flexible film layer between the upper and lower edges of said flexible film layer.

3. The undergarment according to claim 1, wherein said flexible film layer is formed with a plurality of perforated lines which are transversely spaced apart from one another and extend between the vicinity of the upper edge and the vicinity of the lower edge, said flexible film layer being easily torn apart along said perforated lines to form said slits in said flexible film layer.

4. The undergarment according to claim 1, wherein said flexible film layer is bonded to said front waist region by means of a plurality of adhesive stripes that are transversely spaced apart from one another and extend longitudinally of the undergarment.

5. The undergarment according to claim 1, wherein the undergarment further comprises a liquid-pervious topsheet, liquid-impervious backsheet, and a liquid-absorbent core disposed between said liquid-pervious topsheet and said liquid-impervious backsheet.

* * * * *